(12) United States Patent
Hansen

(10) Patent No.: US 7,916,035 B2
(45) Date of Patent: Mar. 29, 2011

(54) DEVICE FOR A BED ALARM

(76) Inventor: Ole Hansen, Gothenburg (SE)

( * ) Notice: Subject to any disclaimer, the term of this patent is extended or adjusted under 35 U.S.C. 154(b) by 284 days.

(21) Appl. No.: 11/915,772

(22) PCT Filed: May 31, 2006

(86) PCT No.: PCT/SE2006/000635
§ 371 (c)(1), (2), (4) Date: Nov. 28, 2007

(87) PCT Pub. No.: WO2006/130081
PCT Pub. Date: Dec. 7, 2006

(65) Prior Publication Data
US 2009/0289800 A1  Nov. 26, 2009

(30) Foreign Application Priority Data
May 31, 2005  (SE) ....................................... 0501240

(51) Int. Cl.
*G08B 23/00* (2006.01)
(52) U.S. Cl. ................. 340/573.1; 340/666; 73/862.041
(58) Field of Classification Search ............... 340/573.1, 340/573.4, 666–668, 506; 73/862.041
See application file for complete search history.

(56) References Cited

U.S. PATENT DOCUMENTS

| | | | |
|---|---|---|---|
| 5,159,316 A | 10/1992 | Lazzara | |
| 5,796,059 A | 8/1998 | Boon | |
| 5,844,488 A | 12/1998 | Musick | |
| 5,898,564 A | 4/1999 | Mayer et al. | |
| 6,217,983 B1 | 4/2001 | Alam et al. | |
| 6,276,054 B1 | 8/2001 | Cartmell et al. | |
| 6,297,738 B1 | 10/2001 | Newham | |
| 6,407,556 B1 | 6/2002 | Rudeke | |
| 6,498,652 B1 * | 12/2002 | Varshneya et al. | 356/477 |
| 6,840,117 B2 * | 1/2005 | Hubbard, Jr. | 73/862.041 |
| 7,319,400 B2 * | 1/2008 | Smith et al. | 340/573.1 |
| 2001/0024712 A1 | 9/2001 | Kirjavainen et al. | |
| 2002/0070866 A1 | 6/2002 | Newham | |
| 2003/0136201 A1 | 7/2003 | Hubbard | |
| 2003/0216670 A1 | 11/2003 | Beggs | |
| 2004/0201487 A1 | 10/2004 | Benson et al. | |
| 2008/0109964 A1 * | 5/2008 | Flocard et al. | 5/713 |

FOREIGN PATENT DOCUMENTS

| | | |
|---|---|---|
| GB | 2322464 A | 8/1998 |
| JP | 56151331 A | 11/1981 |
| SE | 465695 B | 10/1991 |
| SE | 511349 C2 | 9/1999 |
| SE | 512477 C2 | 3/2000 |

* cited by examiner

*Primary Examiner* — John A Tweel, Jr.
(74) *Attorney, Agent, or Firm* — Brooks Kushman P.C.

(57) ABSTRACT

The invention relates to a device (1) for an alarm (2) intended for beds (3) and similar locations that, e.g., old people, demented or handicapped persons are arranged to stay on and that is formed of a sensor (7) distributed on the bed and coupled to a monitoring unit (6) that is arranged to provide alarming. The sensor (7) is arranged to co-operate with a radio receiver (9), positioned remotely from the sensor (7), via radio communication, and is formed of a unit that is arranged to measure the difference of the capacitance of a medium in a compressed and in a free state, respectively. The sensor (7) is formed of a compressible plastic core having a conductive gel applied on at least one side thereof and that is covered, on each side, by an electrode each.

8 Claims, 3 Drawing Sheets

Figure 1:
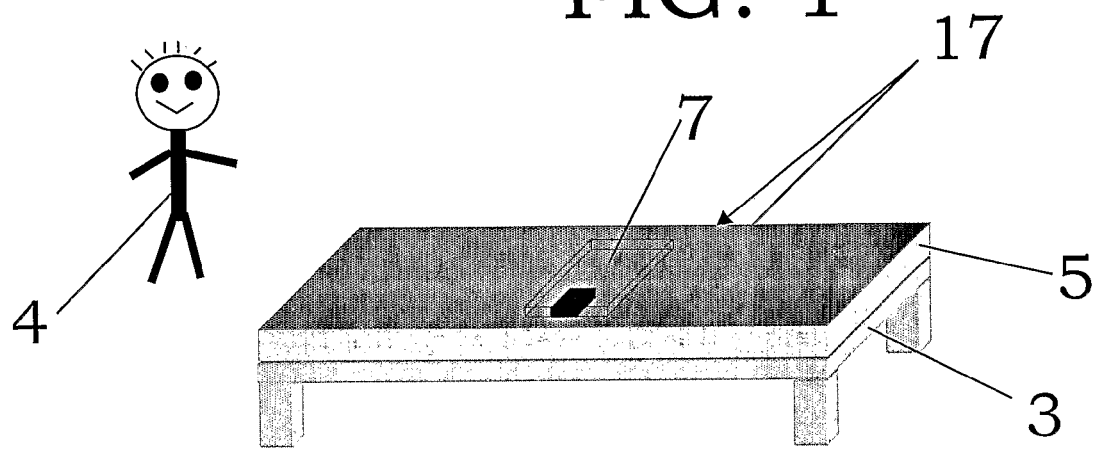

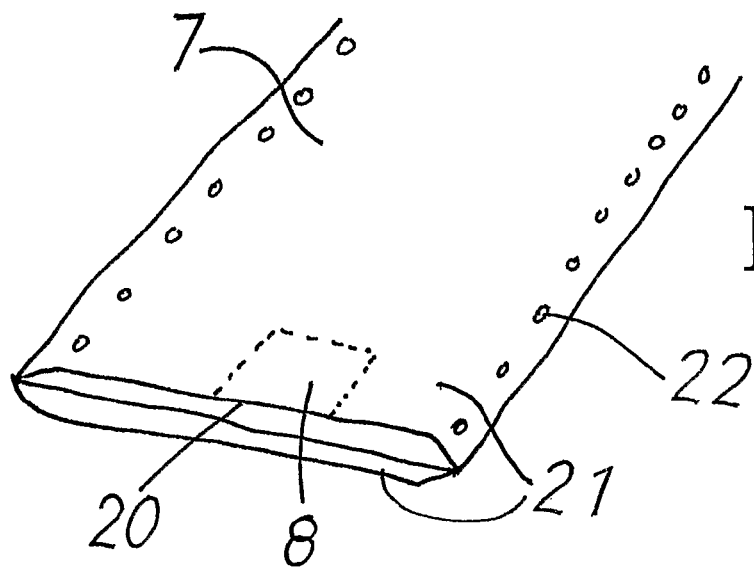
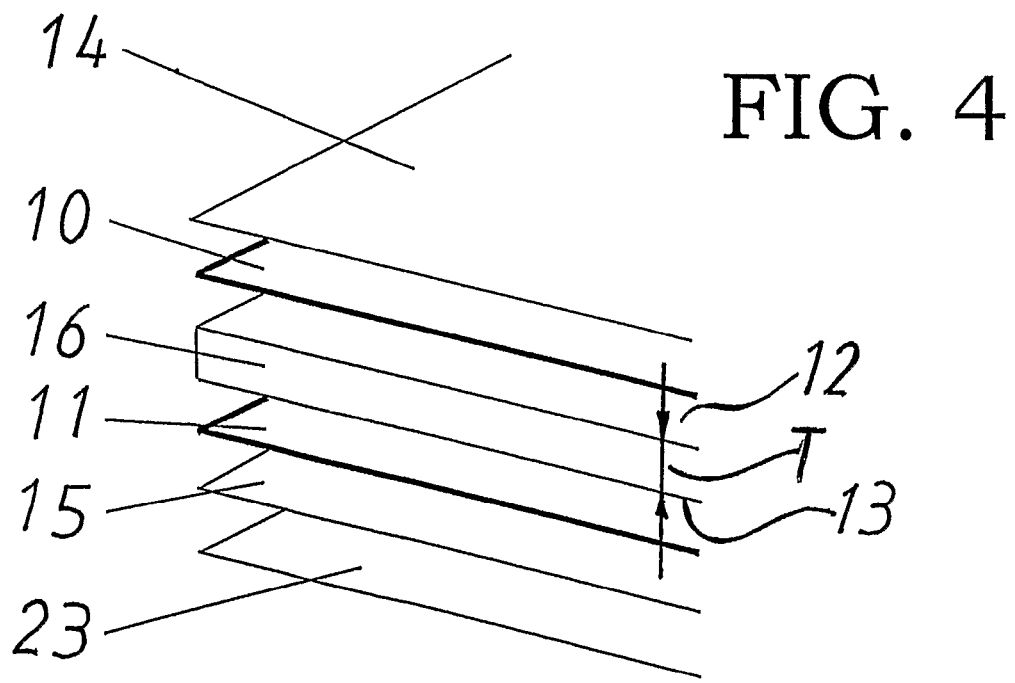

DEVICE FOR A BED ALARM

The present invention relates to a device for an alarm intended for beds and similar locations that, e.g., old people, demented or handicapped persons are arranged to stay on and that comprises a sensor placed on the bed and coupled to a monitoring unit that is arranged to provide alarming.

During the last fifteen years, there have appeared a number of different so-called "Bed guards" or bed alarms on the market. The bed alarms are foremost used in the care of elderly, demented and handicapped persons in hospitals, nursing homes and other similar locations where a plurality of persons reside simultaneously and are monitored and nursed by the staff, and also in private housing where a person receiving care is nursed by some relative or by the staff from the home-help service or home nursing. Said alarm works in such a way that when a person leaves his/her bed and does not lie down again within a desired delay time set beforehand on the alarm, the alarm will be triggered and communicate the staff of this.

The settable delay time is intended to give the person receiving care a certain space of time with the possibility of, e.g., going to the toilet, etc. This desired time delay can be predetermined by the nurses and be set on the alarm device. If this time is exceeded, the alarm is arranged to be possible to be activated and signal to the nurse, who thereby becomes aware of the fact that something may have happened to the person receiving care and may come to the location and check.

If the delay time is set to a very short time, the alarm may also work as fall protection and is activated for alarming as soon as the person in the bed has or is in the intended position to leave the bed or another location it is used for. Thereby, the staff can be alerted fast and prevent that the patients risk falling and getting hurt.

By, for instance, SE 465 695 C2 and SE 512 477 C2, variants of bed alarms are known and that are formed of so-called bed guards including a pressure sensor, which is intended to be placed in the bed of the person receiving care. By means of a box, the alarm is coupled to a remote unit and that contains, among other things, the requisite electronics for, among other things, allowing setting of the desired delay time of the alarm. However, it has turned out that the above-mentioned types of bed guards are not so expedient, since the sensor of the alarms has to be placed on top of the mattress of the bed and that the person receiving care then senses that there is something strange and uncomfortable in the bed. Simultaneously, the staff has to place the sensor in the bed on the exactly correct location upon each bedmaking occasion, and all the occurring flexes that lead from the sensors to the occurring electronic box and further to a free outlet and finally to the existing alarm system, are experienced as troublesome and tangling by the staff. Furthermore, the signal processing in known alarms is such that also upon setting of the shortest delay time, it may take up to 10-12 s before the alarm is activated and a signal arrives to the nurse. This entails a great risk of the patient getting hurt due to fall accidents.

However, by US 2001/0024712 A1, bed guards have appeared similar to the above-mentioned type, but that are arranged to be placed under the mattress, the drawbacks for the person receiving care and for the staff then being avoided. However, these sensors are originally intended for other purposes than the above-mentioned ones. Hence, the suitability of utilizing the same in this context can be debated, and also these type of sensors are wired and provided with a plurality of cords that may tangle.

The above-mentioned "bed guards" are also available in an implementation as a so-called "seat guard". However, in that connection, they differ in the implementation from the bed guard and it can therefore be regarded to be two different products having different functions.

There are also tread mats in order to provide immediate alarm when the person receiving care leaves the bed, and this means that three different products are marketed in order to solve a situation each instead of one and the same product being able to solve all situations simultaneously.

Furthermore, a type of bed guard intended to be placed under the mattress is previously known. It is available in an implementation for wireless signal transfer, but has, however, limited application because it is arranged to work only in combination with the manufacturer's own receivers. Simultaneously, the electronics is difficult to access and the programming is cumbersome. The sensor weighs approx. 1.5 kg and thus is heavy, large and ungainly.

Other variants of bed guards or alarms are available, where the sensor is placed outside the bed. These sensors may be different types of tread mats or movement detectors that are arranged to be placed on the floor in front of the bed of the person receiving care. However, these known bed guards are not so expedient, since they have to be exactly placed to be functioning. By the influence of the person receiving care and also by the staff when cleaning and bed-making, they may easily come out of the desired position and hence cease to work efficiently and safely. Neither can said type of bed guards be provided with a desired delay.

A known variant of alarms is based on optics. However, it is fairly expensive and is very complicated to program, which is not very suitable in a nursing and care environment under stress.

U.S. Pat. No. 5,844,488 A relates to a bed guard that has both a direct alarm function with only a few second's delay and a function with a longer settable delay for, e.g., visiting the toilet, etc. The sensor for said known bed guard is also intended to be placed on top of the mattress in the bed, including all the associated drawbacks this means for the person receiving care as well as the staff/nurse.

US 2003/0136201 A1 is a "sensor sheet" consisting of two sheeting layers having a number of capacitive sensor elements placed therebetween. This means that the sensor should cover the entire bed with a size of approx. 1×2 m, and has to be placed on top of the mattress and in direct contact with the patient. The sensor elements have a thickness of approx. 1.3 cm and are connected by cables. Taken together, a sensor of this type will entail the following disadvantages;
1. The patient senses the sensor elements and cables.
2. The system will be disabled upon bedwetting.
3. The staff contacts the sensor upon each bed-making with the risk of damaging the sensor.
4. The size of the sensor makes it hard to handle.

US 2002/0070866 A1 is constructed as a mattress cover having two capacitive sensors "embedded" in the material. The disadvantages of this construction are generally the same as according to the above.

U.S. Pat. No. 5,796,059 A does not disclose a capacitive sensor, but a contact sensor (pressure sensitive switch) (column 1, line 51 and column 1, lines 60-65).

The plastic layer (18) is not of a porous material, but of a flexible perforated (apertures or openings) material; e.g., PVC (column 3, lines 60-65).

That is, the conductive foam should not penetrate into the non-porous flexible material, but penetrate the material (provide a passage way) (column 3, line 65) and provide contact with the conductive surface layer of the abutment surface (14) and in such a way establish a closed circuit (column 4, lines 1-10).

That is, U.S. Pat. No. 5,796,059 A possesses precisely the weaknesses and limitations that are mentioned above for this type of sensors, in that they give rise to false alarms.

What is more, this sensor is limited in that it is not universal as regards the weight of the persons it should be used by, but has to be manufactured in different implementations (column 4, lines 10-18).

Thus, none of the sensors above works entirely satisfactory. That is, there is a need for a new type of sensor without the disadvantages above.

Hence, the object of the present invention is to construct a bed sensor that does not possess the above-mentioned disadvantages.

This can be provided by constructing a pressure sensor according to the present invention and that is small and can be placed under the mattress to safely detect if a person is present in a bed or has left the bed. The problem that is solved here is that the mattress by itself carries and distributes the pressure from a person lying on the mattress.

By utilizing flexible polyurethane foam of a certain thickness as a dielectric in a capacitive sensor that is placed approximately in the centre under the mattress, it is possible to bring about that the sensor "intercept" the pressure from a person through the mattress.

Since polyurethane foam has a low dielectric constant and since the dielectric cannot be too thick, such a sensor would need to have a fairly large area.

This may be remedied by increasing the active surface of the electrodes.

In turn, this may be accomplished by the fact that a flexible conductive mass penetrates the porous surface of the polyurethane foam.

Both US 2003/0136201 A1 and US 2002/0070866 A1 are fairly unwieldy and are almost to be compared to fixed installations for use in hospitals for the monitoring of patients, and where US 2003/0136201 A1 is able to do more than only detect presence non-presence: "position, agitation, seizure activity respiration etc". US 2003/0136201 A1 and US 2002/0070866 A1 are only intended to be used in a bed and can, due to the size, not be placed in a chair.

There is need for simple solutions intended to be installed in different types of homes designed for the elderly, which are easily handled and readily can "be installed" by the staff frequently under stress in order to be easily movable from one patient to another and from, e.g., a bed to a chair.

Thus, neither individually nor in combination it is seen from the above-cited publications any such presently defined device and pressure sensor, respectively, that are defined in the new claims, and what is defined in said claims can neither be regarded as obvious for a person skilled in the art.

Finally, capacitive pressure sensors are previously known by SE 511349 C2 and U.S. Pat. No. 5,159,316 A. However, it is not very likely that said known sensors are suitable or at all can work as sensors in a bed-guard system.

The main object of the present invention is primarily to provide a device for an alarm that is intended for beds and similar locations and that allows to solve, among other things, the above-mentioned problems in an efficient and safe way.

Said object is attained by means of a device according to the present invention, which substantially is characterized in that the sensor, which is arranged to be placed under the mattress of the bed, is arranged to co-operate with a radio receiver, positioned remotely from the sensor, via radio communication, that the sensor is arranged to measure the difference of the capacitance of a medium in a compressed and in a free state, respectively, that the sensor comprises a compressible plastic core of a flexible, porous plastic material having a porous surface, e.g., foam plastic, preferably polyurethane foam plastic, that a conductive gel is applied to cover both sides of the plastic core and arranged to penetrate into the mass of the porous foam, and that the conductive gel is covered, on each side, by an electrode.

Figure 2:
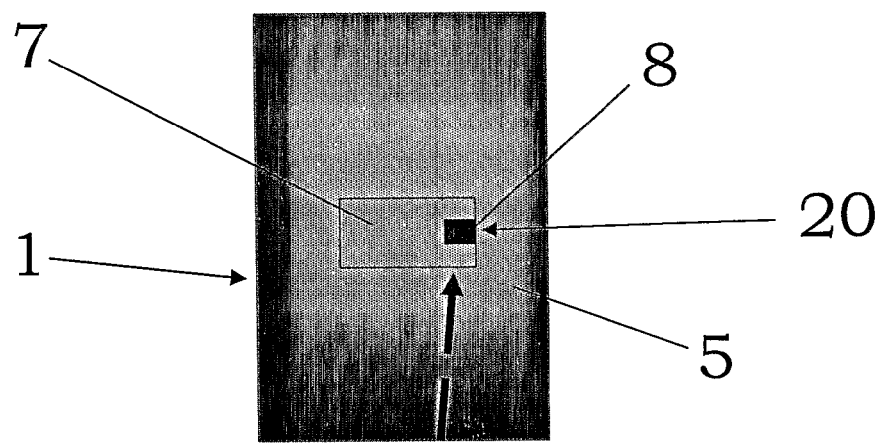

The invention is described in the following in the form of a preferred embodiment example, reference being made to the accompanying drawings, in which FIG. 1 shows the device applied in a bed, FIG. 2 schematically shows parts included in the alarm, FIG. 3 shows a part of a pressure-sensitive capacitive sensor in perspective, and FIG. 4 shows a part of the sensor in an exploded view.

Figure 5:
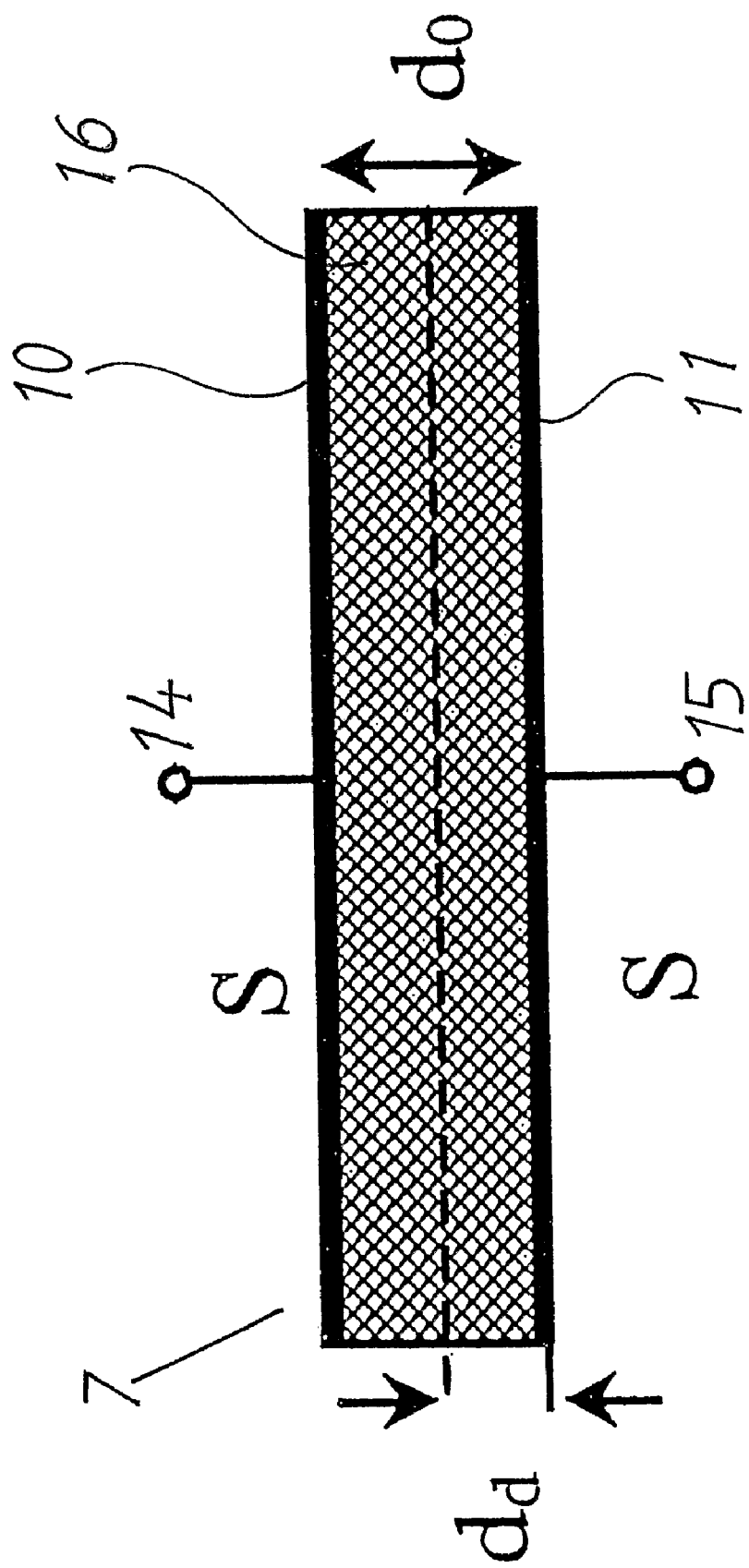

FIG. 5 shows a cross section of the sensor.

A device 1 for an alarm 2 that primarily is intended for beds 3 and similar locations that, e.g., old people 4, demented or handicapped persons are arranged to stay on and that is formed by a sensor 7 distributed on the bed 3 and coupled to a monitoring unit 6 and that is arranged to provide alarming on desired occasions, comprises, according to the present invention, a sensor 7 and a radio-transmitter unit 8.

More precisely, the sensor 7 is arranged to co-operate with a radio receiver 9, positioned remotely from the sensor 7, via radio communication, and that the sensor 7 is formed of a unit that is arranged to be able to measure the difference of the capacitance of a medium in a compressed and in a free state, respectively. Said sensor 7 is formed of a compressible plastic core 16 having a conductive gel 10, 11 applied on at least one side 12, 13 thereof and that is covered, on each side, by an electrode 14, 15 each.

The invention is a bed guard that consists of a pressure-sensitive capacitive sensor 7 and an external electronic unit denominated "the room module" 9. In the sensor, there is electronics 20, with, among other things, the transmitter 8 and a battery, built-in and that via a transceiver is arranged to communicate with the room module 9. It is also arranged to check that communication is maintained according to the principle "I'm here, I'm alive".

The room module 9 is the interface to the user and has controls for the choice of function and setting of the desired delay time, switching on and off as well as reset after alarm.

According to a first embodiment example, only one side 12 of the sensor 7 is covered with a conductive gel 10, while according to a second embodiment example, also the other side 13 of the sensor 7 is covered with conductive gel 11.

The function of the pressure sensor is based on the measurement of the difference of the capacitance of a medium when it is in a compressed state and in a free, stretched state, respectively, and that thereby detection is accomplished whether a weight is applied to the medium or if it is unloaded.

Said medium is a plastic core 16, which is formed of a flexible, porous plastic material having a porous surface, a foam plastic and preferably polyurethane foam plastic. Said polyurethane foam plastic has a thickness T between 4 and 12 mm or even more.

The function of the pressure sensor is based on the measurement of the difference between the capacitance of a medium when it is in a compressed state and not affected by any load, respectively, and thereby detecting if any load is applied to the medium or not. Since the medium 16 is flexible and is formed of a porous plastic material having a porous surface, preferably polyurethane foam plastic, the load cases can easily be detected.

The conductive gel 10, 11 is arranged to be penetrated into the mass of the porous foam. Preferably, polyurethane foam was used since that material is inexpensive and is commercially available in a number of different grades in order to match the porosity, hardness and flexibility of said medium 16. Thereby, it becomes possible to adapt the medium 16 according to different applications considering the weight to be detected.

The electrodes 14, 15, which cover the gel 10, 11 in question, are preferably formed of aluminium foil and/or aluminium/polyester laminate.

The conductive gel 10, 11 is either ion conductive or electron conductive and is formed of an adhesive flexible film, which after the application cures into a mechanically stable, rubber-like mass.

In principle, the pressure sensor 7 is a capacitor and the polyurethane foam acts as a dielectric. The pressure sensor is distinguished by a conductive gel 10, 11 being applied to, e.g., the top side and underside 12, 13 of the medium 16 and that penetrates into the porous surface of the foam. The opposite out-turned surface of said gel 10, 11 contacts connecting electrodes 14, 15 of flexible copper or aluminium foil, e.g., copper/polyester laminate and/or aluminium/polyester laminate, which is applied farthest out on the sensor 7 and which substantially increases the active surface of the electrodes, and thereby also increases the measurable difference in capacitance when the medium 16 is under compressive load and the distance between the two active surfaces decreases. By the application of the conductive gel, it becomes possible, by means of a sensor that has a relatively small surface, e.g., 22 times 46 cm including surrounding casing, to efficiently sense the pressure from a person 4 who lies down on a bed mattress 5 and, accordingly, also sense when the person 4 in question rises from the bed 3. The device 1 has electronics that is arranged to transform the measured quantities into a signal that is transmitted to the room module 8 in question.

The sensor 7 is contained in a circumferential casing 21 having air holes 22 along the edges thereof. A stiffer and robust bottom 23, which is arranged to protect the sensor from being damaged by springs or other hard objects that may be found in the frame of the bed, may be arranged on the underside of the sensor. For instance, said bottom may be formed of a polyester foil. The bed alarm 2 is further distinguished by the fact that the pressure sensor 7, in combination with the room module 9, is a multifunctional alarm unit having three different functions, which usually require three different alarm modules to be executable.

The pressure sensor 7 will be included in a concept of passive alarm modules for the care of elderly and demented. Here, it may advantageously replace existing bed guards in that it may be placed under the mattress without any wiring being needed. The signal goes to a unit, the room module, which contains required electronics and which may be placed anywhere in the room and be coupled to existing alarm system, or by means of a built-in radio unit transmit the alarm forward to a portable unit hold by the staff or a relative/nurse.

The pressure sensor will have three functions;

I. When it is placed in the centre under the upper half of the mattress 5, it will act as a bed guard with delay time, i.e., it is entered an adjustable interval from when a person 4 has left the bed until the alarm is triggered.

II. When it is placed under the mattress 5 along one side 17 of the bed, it will operate with "instant alarm". That is, when the person 4 in the bed 3 moves his/her weight toward the side 17 of the bed in order to get up from the bed, the alarm is triggered directly, before the person 4 has had time to leave the bed 3. Thereby, it becomes possible to efficiently prevent fall accidents. If it is not sure from which side the person leaves the bed, two sensors are placed under the mattress along each side of the bed.

III. The sensor may also be placed under a seat cushion in a chair, etc., and acts, in doing so, as a "chair guard".

There are also other application possibilities for this pressure sensor.

Detailed Description of the Capacitive Pressure Sensor

The capacitive pressure sensor consists of a soft dielectric material, which is placed between two metal electrodes. The system has a certain capacitance, which is changed by virtue of mechanical deformation of the dielectric that is the body of the sensor. Thus, the ratio, $k=C_d/C_0$ of the capacitance ($C_0$) before and ($C_d$) after the deformation, is the parameter that informs if a weight is applied to the system.

The examples below demonstrate the performance and effect of different types of sensors.

Type A: The dielectric material should be a flexible, porous plastic material having a porous surface, preferably polyurethane foam. A specimen of polyurethane foam (Recticel B50120, average cell diameter=800 μm, density=120, and specific surface area, $m^2/m^3$=2900) of the size 24×18×0.8 cm is placed between electrodes (aluminium foil) having the area S=432 $cm^2$, see FIG. 5. The capacitance is measured between the electrodes 14 and 15 in two cases: without pressure having been applied (the thickness of the foam is $d_0$=0.8 cm) and under pressure (the thickness of the foam is $d_d$=0.3 cm). The surfaces of the polyurethane foam, which are facing the electrodes, are covered with layers of a conductive gel. This brings the system a unique property by the fact that the active surface of the electrodes is increased substantially. This occurs since the gel penetrates into the mass of the porous foam. An estimation of the depth of the penetration yielded Δ≈0.05 cm. Knowing the surface, S, of the electrodes, the volume of the gel inside the foam was calculated to be $V_{gel}=\Delta \cdot S=0.05 \cdot 432=21.6$ $cm^3$. Furthermore, the active surface of the capacitor was found to be $Q=q \cdot V_{gel}=29 \cdot 21.6=626$ $cm^2$ (here, q=29 $cm^2/cm^3$ is the specific surface of the foam used). With all necessary parameters described, the capacitance $C_0$ and $C_d$ was calculated as:

$$C_0=\epsilon_0 \epsilon_f Q/(d_0-2\Delta)=0.129 \text{ nF}, C_d=\epsilon_0 \epsilon_f Q/(d_d-2\Delta)$$
$$=0.455 \text{ nF}, k=C_d/C_0=3.52$$

The following result was obtained by measurement:
$C_0$=0.125 nF, $C_d$=0.457 nF, $k=C_d/C_0$=3.66

The deviation of the calculated values from the measured ones is 3.2% for $C_0$ and 0.4% for $C_d$. The high functionality of the sensor resides in the notable variation of the capacitance according to the factor k.

Type B: This is like A, but only one side of the sides of the polyurethane foam is covered with the conductive gel. This implies an uncertainty in defining the active surface of the capacitor (one of the sides has the area S=432 $cm^2$ and the other Q=626 $cm^2$).

Calculations made, assuming that the active surface corresponds to Q, yielded:

$$C_0=\epsilon_0 \epsilon_f Q/(d_0-\Delta)=0.121 \text{ nF}, C_d=\epsilon_0 \epsilon_f Q/(d_d-\Delta)$$
$$=0.364 \text{ nF}, k=C_d/C_0=3.00$$

The measured values yielded:
$C_0$=0.095 nF, $C_d$=0.31 nF, $k=C_d/C_0$=3.26

In this case, the deviations are high (27.3% for $C_0$ and 14.8% for $C_d$), based on above-mentioned uncertainties. However, the measured factor k has still a high magnitude, which reflects the high functionality of the method.

The thickness of the polyurethane foam may vary and be between 4 mm and 12 mm and even thicker, however, it must not be thicker than that a person lying in the bed does not sense that there is something under the mattress. The bed guard sensor in question will have a dimension of, for instance, 180×420×8 mm.

It is possible to place several sensors in the same bed if a very light person, e.g., a child, is to be monitored, or if there is possibility for a person to rise up from the bed alternately from both sides.

Detailed Description of the Room Module

The electronics of the room module 8 is distinguished by the fact that it measures the alteration of the capacitance of the pressure sensor to measure said three different functions.

I. Function with delay time: The function selector of the room module is set to this function. When the sensor is located in the centre under the upper half of the mattress and no one is in the bed, the electronics of the room module is in the "neutral" position. When a person is lying down in the bed, the capacitance of the pressure sensor will increase and the electronics of the room module turns into the "alert" position. When the person leaves the bed, the capacitance of the pressure sensor will decrease and the electronics of the room module turns into the "alarm" position, and the relay is activated when the set delay time has been exceeded. If the person lies down again in the bed before the delay time has been exceeded, the electronics will return to the "alert" position.

II. Function "instant alarm": The function selector of the room module is set to this function. When the sensor is located under the mattress along one side of the bed, or along both sides thereof, and no one is in the bed, the electronics of the room module is in the "neutral" position. When a person lies down in the bed, the capacitance of the pressure sensor will increase and the electronics of the room module is set into the "alert" position. When the person moves toward one side of the bed in order to rise, the capacitance of the pressure sensor will increase further, above the "alert" level, and the relay will be activated.

III. Function "chair guard": The function selector of the room module is set to this function. The sensor is located under a seat cushion in a chair and when no one is sitting in the chair, the electronics of the room module is in the "neutral" position. When a person sits down in the chair, the capacitance of the sensor will increase and the electronics of the room module turns into the "alert" position. When the person rises from the chair, the capacitance of the sensor will decrease and the electronics of the room module is directly set into the "alarm" position without delay and the relay is activated.

The electronics of the room module can receive and process signals from a plurality of different sensors.

Description of the Conductive Gel

The conductive gel may be either ion conductive or electron conductive. It should be a thick, adhesive, flexible film of a rubber-like consistency. It should be applied in a layer between the surface of the PU foam and the electrode, and then be sufficiently soft to be able to penetrate the porous surface to a depth of approx. 1 mm. Subsequently, it should cure into a mechanical stable, rubber-like mass so that it, in principle, provides an expansion of the electrode, and in such a way increases the active surface thereof.

The gel should have a resistivity of between $10^{-0}$ and $10^{-7}\Omega^2$, preferably between $10^{-2}$ and $10^{-3}\Omega^2$.

The gel should simultaneously be composed of materials that do not damage the polyurethane foam or in any way lessens the mechanical properties, flexibility and durability thereof.

Suitable materials may be different types of polymer electrolytes similar to those that are used in lithium batteries or different types of carbon black/polymer composites.

In a preferred embodiment, the gel is a carbon black/polymer composite consisting of a cold-curing poly(methyl methacrylate) of the type that is used as bone cement or as tooth filling, e.g., Colacryl TS 1785 from Lucite, and where carbon black of the type Ketjenblack 600 from AkzoNobel is used as conductive filling.

By utilizing propylene carbonate as a softener, it becomes possible to manufacture a two-phase system, where the carbon is dispersed in the propylene carbonate and where the PMMA acts like a sponge, which in principle has absorbed the conductive PC/CB mix. Thus, it becomes possible, with a relatively small fraction of CB, approx. 2.5% by weight of the total amount of composite, to achieve a resistivity of approx. $10^{-2}\Omega^2$.

The invention is naturally not limited to the embodiments described above and shown in the accompanying drawings. Modifications are feasible, particularly as for the nature of the different parts, or by the usage of an equivalent technique, without departing from the protected area of the invention, such as it is defined in the claims.

The invention claimed is:

1. A sensor for an alarm intended for beds and similar locations that, e.g., old people, demented or handicapped persons are arranged to stay on and that comprises a sensor placed on the bed and coupled to a monitoring unit that is arranged to provide alarming, characterized in that the sensor, which is arranged to be placed under a mattress of the bed, is arranged to cooperate with a radio receiver, positioned remotely from the sensor, via radio communication, that the sensor is arranged to measure the difference of the capacitance of a medium in a compressed and in a free state, respectively, the sensor comprising:

a compressible plastic core of a flexible, porous foam plastic material having a porous surface;

a conductive gel applied to cover both sides of the plastic core and arranged to penetrate into the mass of the porous foam; and a pair of electrodes, one located on each side of the plastic core contacting the conductive gel.

2. A sensor according to claim 1, characterized in that the porous foam plastic has a thickness between 4 and 12 mm and is made of polyurethane.

3. A sensor according to claim 1, characterized in that the electrodes are formed of aluminum foil.

4. A sensor according to claim 1, characterized in that the conductive gel is either ion conductive or electron conductive and is formed of an adhesive flexible film, which after the application cures into a mechanically stable, rubber-like mass and has a resistivity of between $10^{-0}$ and $10^{-7}\Omega^2$, preferably between $10^{-2}$ and $10^{-3}\Omega^2$.

5. A sensor according to claim 4, characterized in that the conductive gel is formed of a polymer electrolyte, polymer composite such as carbon black/polymethyl methacrylate.

6. A pressure sensor arranged to detect the pressure from persons who are present on said pressure sensor and that, in combination with an electrical room module for the receipt of information from the sensor, forms an alarm unit, characterized in that the sensor unit comprises a transmitter for the cooperation with the room module, as well as a battery, that the sensor is arranged to cooperate with a radio receiver, positioned remotely from the sensor, via radio communication, that the sensor is arranged to measure the difference of the capacitance of a medium in a compressed and in a free state, respectively, the pressure sensor comprising;

a compressible plastic core of a flexible porous plastic material having a porous surface;

a conductive gel applied to cover both sides of the plastic core and arranged to penetrate into the mass of the porous foam; and a pair of electrodes, one located on each side of the plastic core contacting the conductive gel.

7. A Pressure sensor according to claim 6, characterized in that it is arranged, by the built-in electronics, to be able to measure changes of pressure that arise dependent on where the sensor is located under a mattress, in order to obtain information about if a person is present or not, as well as if a person moves toward the edge of the bed in order to leave the bed.

8. A pressure sensor arranged to detect the pressure from persons who are present on said pressure sensor and that, in combination with an electrical room module for the receipt of information from the sensor, forms an alarm unit, characterized in that the sensor unit comprises a transmitter for the cooperation with the room module, as well as a battery, that the sensor is arranged to cooperate with a radio receiver, positioned remotely from the sensor, via radio communication, that the sensor is arranged to measure the difference of the capacitance of a medium in a compressed and in a free state, respectively, the pressure sensor comprising;

a compressible plastic core of a flexible porous plastic material having a porous surface;

a conductive gel applied to cover both sides of the plastic core and arranged to penetrate into the mass of the porous foam;

a pair of electrodes, one located on each side of the plastic core contacting the conductive gel;

wherein the sensor, owing to the relatively small size thereof, may be arranged to work also as a chair guard, whereby the sensor is arranged to operate multifunctionally.

\* \* \* \* \*